United States Patent
Dai et al.

(10) Patent No.: US 11,369,808 B2
(45) Date of Patent: Jun. 28, 2022

(54) CYSTIC APPLICATOR AND METHOD FOR DETERMINING THICKNESS OF SCATTERING FOIL AND MODULATOR THEREIN

(71) Applicants: Jianrong Dai, Beijing (CN); Pan Ma, Beijing (CN)

(72) Inventors: Jianrong Dai, Beijing (CN); Pan Ma, Beijing (CN)

(*) Notice: Subject to any disclaimer, the term of this patent is extended or adjusted under 35 U.S.C. 154(b) by 100 days.

(21) Appl. No.: 16/360,919

(22) Filed: Mar. 21, 2019

(65) Prior Publication Data
US 2019/0290936 A1 Sep. 26, 2019

(30) Foreign Application Priority Data
Mar. 22, 2018 (CN) .......................... 201810244336.0

(51) Int. Cl.
*A61N 5/10* (2006.01)
*G01B 15/02* (2006.01)

(52) U.S. Cl.
CPC .......... *A61N 5/1084* (2013.01); *A61N 5/1045* (2013.01); *G01B 15/025* (2013.01); *A61N 2005/1089* (2013.01); *A61N 2005/1095* (2013.01)

(58) Field of Classification Search
CPC .......... A61N 5/1045; A61N 2005/1089; A61N 5/1042; A61N 5/1084; A61N 2005/1095; A61N 2005/1096; A61N 2005/1091; G01B 15/025
See application file for complete search history.

(56) References Cited

U.S. PATENT DOCUMENTS

| | | | |
|---|---|---|---|
| 2008/0267352 A1* | 10/2008 | Aoi ........................ | H05H 7/02 378/65 |
| 2013/0221243 A1* | 8/2013 | Perkins ................ | A61N 5/1042 250/492.3 |
| 2014/0206925 A1* | 7/2014 | Gerard ................. | A61N 5/1015 600/7 |
| 2014/0266208 A1* | 9/2014 | Dempsey ........... | G01R 33/4808 324/322 |
| 2015/0085993 A1* | 3/2015 | Scheib ................. | A61N 5/1049 378/207 |
| 2016/0310764 A1* | 10/2016 | Bharadwaj ............. | H05H 9/048 |

FOREIGN PATENT DOCUMENTS

WO    WO-2017151763 A1 * 9/2017   ........... A61N 5/1067

* cited by examiner

*Primary Examiner* — Christine H Matthews
*Assistant Examiner* — Joshua Daryl D Lannu

(57) ABSTRACT

The present disclosure generally relates to an applicator for radiotherapy and a method for determining a thickness of a scattering foil and modulator therein. According to one embodiment, an applicator for radiotherapy may comprise a housing having a hollow structure with an opening, a scattering foil disposed at an opening of the hollow structure and configured to receive a first radiation and convert a portion of the first radiation into a second radiation while scattering the first radiation, and a modulator disposed inside the hollow structure and configured to modulate an intensity of mixed radiation including the first radiation and the second radiation.

12 Claims, 7 Drawing Sheets

CYSTIC APPLICATOR AND METHOD FOR DETERMINING THICKNESS OF SCATTERING FOIL AND MODULATOR THEREIN

CROSS-REFERENCE TO RELATED APPLICATION

This application claims the benefit of Chinese Patent Application No. 201810244336.0 filed Mar. 22, 2018. The aforementioned nonprovisional application is hereby incorporated by reference for all purposes

TECHNICAL FIELD

The present invention generally relates to the field of radiotherapy, and more particularly to a cystic applicator for radiotherapy and a method for determining a thickness of a scattering foil and a modulator therein.

BACKGROUND

An electron beam is one of the radiation sources used in tumor radiotherapy, and it is mostly used in intraoperative radiotherapy (Intra-Operative Radiotherapy, IORT) for an abdomen (e.g. liver, pancreas, etc.) tumor and external beam radiotherapy of a superficial tumor with a plane distribution. For IORT of a spherical cystic tumor (e.g., surgical tumor bed for breast cancer and brain tumor) and intracavitary treatment of a tubular tumor (e.g., vaginal cancer, oral cancer, etc.), the current electron beam irradiation technology cannot realize irradiation of a non-planar dose distribution.

SUMMARY

In order to better apply the electron beam to radiotherapy, the present disclosure provides a cystic applicator which may be used for electron beam radiotherapy and a design method thereof, more specifically, a method for determining a thickness of a scattering foil and a modulator in a cystic applicator. The cystic applicator of the present disclosure may convert a portion of an electron beam into X-rays, and modulate an intensity of mixed radiation of the electron beam and X-rays, forming a uniform dose distribution in a region outside a surface of the cystic applicator and being used for radiotherapy of a cystic tumor (including a spherical cystic shape, a tubular shape and any other cystic tumors), thus expand the application field of the electron beam radiotherapy.

According to an exemplary embodiment, disclosed is a cystic applicator for radiotherapy, comprising: a housing having a hollow cystic structure with an opening; a scattering foil disposed at the opening of the hollow cystic structure and configured to receive first radiation and convert a portion of the first radiation into second radiation while scattering the first radiation in a large spread angle; and a modulator disposed inside the hollow cystic structure and configured to modulate an intensity of mixed radiation including the first radiation and the second radiation.

In some embodiments, preferably, the scattering foil has a thickness that is optimized to ensure that the first radiation has a predetermined scattering angle while the mixed radiation has a predetermined intensity.

In some embodiments, preferably, the modulator has a thickness that is optimized so that the mixed radiation has a desired intensity distribution on an outer surface of the housing.

In some embodiments, the first radiation is electron beam radiation and the second radiation is X-ray radiation.

In some embodiments, the housing comprises a rigid soft-tissue-equivalent material to support the scattering foil and the modulator.

In some embodiments, the hollow cystic structure comprises a spherical cystic shape, a tubular cystic shape, or an irregular cystic shape corresponding to a tumor region to be irradiated.

In some embodiments, the cystic applicator further comprises a collimator connected to the opening of the housing, the first radiation being irradiated onto the scattering foil through the collimator.

In some embodiments, the collimator and the housing are formed as an integrated structure.

In some embodiments, an outer surface of the modulator contacts an inner surface of the housing.

In some embodiments, an outer surface of the modulator is spaced apart from an inner surface of the housing.

In some embodiments, the scattering foil comprises a material with a high atomic number that may produce an X-ray within a larger scattering angle range.

In some embodiments, the thickness of the scattering foil is optimized to ensure that an X-ray is generated within a larger scattering angle range while sufficient intensity of the mixed radiation is still maintained and thus a higher dose rate is maintained.

In some embodiments, the modulator interacts with the mixed radiation passing through the scattering foil to modulate the intensity of the mixed radiation.

In some embodiments, the modulator includes a material of a low atomic number that may modulate an X-ray intensity but is difficult to generate a photoelectron.

In some embodiments, the thickness angle distribution of the modulator is optimized to modulate the intensity of the mixed radiation to produce a uniform dose distribution in a region outside the surface of the cystic applicator.

According to another exemplary embodiment, provided is a method for determining a thickness of a scattering foil in a cystic applicator, comprising: disposing N scattering foils at an opening of a hollow cystic structure, in order to convert a portion of first radiation to second radiation while scattering the first radiation in a large angle range, where N is zero or a positive integer and each scattering foil has a predetermined thickness; determining a scattering angle of the first radiation corresponding to each scattering foil in a plane directly below the scattering foils; determining a radiation intensity corresponding to each scattering foil at an intersection point of the plane directly below the scattering foils and a central axis of the hollow cystic applicator; and selecting an appropriate thickness of the scattering foil to maintain a predetermined intensity of the mixed radiation while the first radiation has a predetermined scattering angle.

According to another exemplary embodiment, provided is a method for determining a thickness of a modulator in the above-mentioned cystic applicator, comprising: providing the cystic applicator without the modulator; stacking N adjustment layers in the housing of the cystic applicator to adjust an intensity of the mixed radiation, where N is zero or a positive integer and each adjustment layer has a predetermined thickness; measuring the intensity of the mixed radiation at a plurality of points on an outer surface of the housing of the cystic applicator to determine a relation between the intensity of the mixed radiation and the thickness of the adjustment layer at each point; determining a target thickness of the adjustment layer at each point corresponding to a desired mixed radiation intensity based on the relation; and determining a thickness of the modulator at each point based on the target thickness of the adjustment layer.

In some embodiments, the adjustment layer and the modulator are made of the same material, and the thickness of the modulator is equal to the target thickness of the conditioning layer at each point.

The present disclosure has the following beneficial effects: by implementing the method, a portion of the electron beam can be converted into X-rays, and an X-ray intensity can be modulated, generating a uniform dose distribution in a region outside the surface of the cystic applicator, and being used for radiotherapy of the cystic tumor (including a spherical cystic tumor, a tubular tumor and any other cystic tumors), thus the application range of electron beam can be expanded.

Other features and advantages of the application will be set forth in the following description, and will be obvious in part from the description, or be understood through the implementation of the present application. The purpose and other advantages of the present application may be achieved and attained by the structures particularly pointed out in the specification, claims, and drawings.

DESCRIPTION OF EMBODIMENTS

Figure 1:
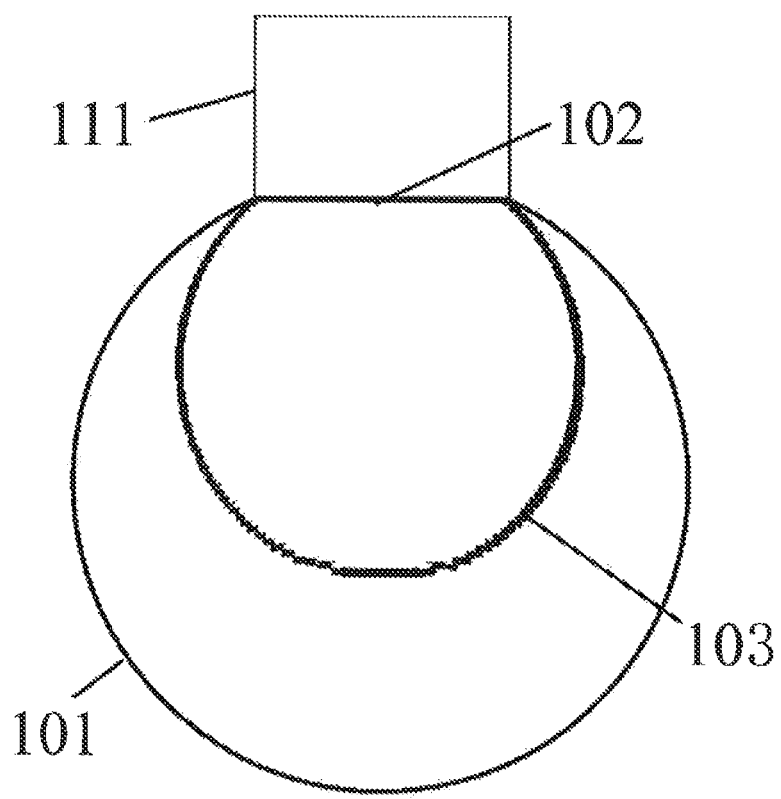
FIG. 1 is a schematic structural diagram showing a cystic applicator according to an exemplary embodiment of the present disclosure.

Hereinafter, an exemplary embodiment according to the present disclosure will be described in detail with reference to the drawings. Here, it should be noted that in the drawings, the same reference signs are assigned to components having substantially the same or similar structures and functions, and repeated descriptions thereof will be omitted. In addition, it should be noted that the drawings may not be drawn to scale. Obviously, the described embodiments are only a portion of the embodiments of the present disclosure and not all the embodiments of the present disclosure, and it should be understood that the present disclosure is not limited by the exemplary embodiments described herein.

FIG. 1 is a schematic structural diagram showing a cystic applicator according to an exemplary embodiment of the present disclosure. As shown in FIG. 1, a cystic applicator comprises a housing 101, which may be a hollow cystic structure and has an opening. The hollow cystic structure may be any shape, such as, but not limited to, a spherical cystic shape, a tubular cystic shape, or an irregular cystic shape corresponding to a tumor region to be irradiated, for simplicity and convenience, a spherical cystic is shown here. The material of housing 101 may be a soft-tissue-equivalent material, and it is rigid and has strong hardness to support structures such as a scattering foil 102 and a modulator 103 described below, and may support a tumor region surrounding the housing. In one example, the housing may be made of plexiglass, PMMA, plastic, polyester, etc.

The cystic applicator further comprises a scattering foil 102 disposed at the opening of the housing 101. The scattering foil 102 may receive and scatter first radiation from a radiation head (not shown), such as an electron beam, and convert a portion of the first radiation into second radiation, such as an X-ray. Since the scattering angle of interaction between high-energy electrons and the material is proportional to the square of atomic number of material and proportional to the thickness of the material, therefore, for an electron beam from a single direction, a larger scattering angle is required in order to produce a uniform dose distribution in a region outside a surface of the cystic applicator, therefore, the material of scattering foil 102 may be selected from a material with a high atomic number, such as tungsten. On the other hand, increase of the thickness of the scattering foil 102 may also increase the scattering angle, but the larger the thickness of the scattering foil 102, the lower the dose rate of radiation, therefore, the thickness of the scattering foil 102 needs to be optimized to ensure that sufficient scattering rays are generated within a larger scattering angle range while maintaining a higher dose rate.

The method for determining the thickness of the scattering foil 102 in the cystic applicator according to an exemplary embodiment of the present disclosure are as follows: in a first step, disposing different numbers (e.g., 0, 1, 2, . . . , 10, and more) of scattering foils at the opening of the hollow cystic structure, and the thickness of the scattering foils increases by 0.1 mm one by one from 0 mm; in a second step, determining electron beam scattering angles corresponding to the different numbers of the disposed scattering foils in a plane directly below the scattering foils; in a third step, determining a radiation intensity corresponding to different numbers of the disposed scattering foils at an intersection point of the plane directly below the scattering foils and a central axis of the hollow cystic applicator; in a fourth step, selecting an appropriate thickness of the scattering foil to maintain a higher dose rate while ensuring that sufficient scattering rays are generated within a larger scattering angle range. Thus, the thickness of the scattering foil is determined. In an exemplary embodiment, the dose rate is about 50 cGy/min. Determining an electron beam scattering angle and an intensity of the mixed radiation may be performed by various methods, for example, it may be performed by a physical measurement or may also be performed by a simulation calculation. For example, under the condition of attenuation and scattering of each scattering foil, a Monte Carlo simulation method may be used to calculate the scattering angle and dose. In one exemplary embodiment, the thickness of the scattering foil 102 may be in a range of 0.1-2 mm, for example, about 0.5 mm.

The shape of the scattering foil 102 is the same as that of the opening of housing 101, which enables the electron beam to interact with substance of the scattering foil. In one embodiment, the electron beam is a 6 MeV electron beam passing through a circular cylindrical collimator 111 with a diameter of 20 mm, and the shape of the scattering foil 102 is a circle with a diameter of 20 mm. In order to maintain a high dose rate, the thickness of the scattering foil 102 converts only a portion of electrons into X-rays, and after the electron beam enters the scattering foil 102 and interact with the scattering foil 102, the obtained radiation beam is a mixed beam, which includes both X-rays and electrons.

Continuing referring to FIG. 1, the cystic applicator further comprises a modulator 103, which is disposed inside the interior of the housing 101. It should be understood that in the example of FIG. 1, the housing 101 is a hollow spherical structure with an opening, and the modulator 103 is disposed to cling to an inner wall of the housing 101, i.e. in FIG. 1, the housing is schematically shown by a solid line 101, and the region between solid lines 101 and 103 is a modulator, and the solid line 103 is an inner surface of the modulator. The modulator 103 is used to modulate the intensity of the mixed radiation including the first radiation, such as the electron beam, and the second radiation, such as the X-ray, and it may be made of a material with a low atomic number that may modulate the intensity of the mixed beam but is difficult to generate a photoelectron. It is well known that, for a particular material, the greater the thickness thereof, the greater the attenuation for radiation. In order to realize a uniform intensity distribution on the surface of the housing 101, the modulator 103 is needed to have a desired thickness at each position. For example, if the intensity at a certain position is high, the modulator 103 is needed to be disposed thicker, and if the intensity at a certain position is low, the modulator 103 is needed to be disposed thinner, finally a uniform intensity distribution is realized. In some embodiments of the present disclosure, the modulator 103 has an optimized thickness so that the mixed radiation has a desired intensity distribution, such as a uniform intensity distribution, on an outer surface of the housing 101, which may of course be other non-uniform intensity distributions according to actual application requirements. The optimization method of the thickness of modulator is described below.

The cystic applicator shown in FIG. 1 may further comprise a collimator 111 connected to the opening of the housing 101. An electron beam may be irradiated onto the scattering foil 102 through the collimator 111. The material of the collimator 111 may be plexiglass, and the thickness of collimator wall may be 5 mm. In the example of FIG. 1, the collimator 111 and the housing 101 are formed as an integrated structure, which is convenient to maintain the position of the scattering foil 102 and the modulator 103 relative to the electron beam in the cystic applicator, thus maintaining radiation features. In addition, the integral design is also convenient to simplify the clinical operation process and shorten the time of radiotherapy.

Figure 2:
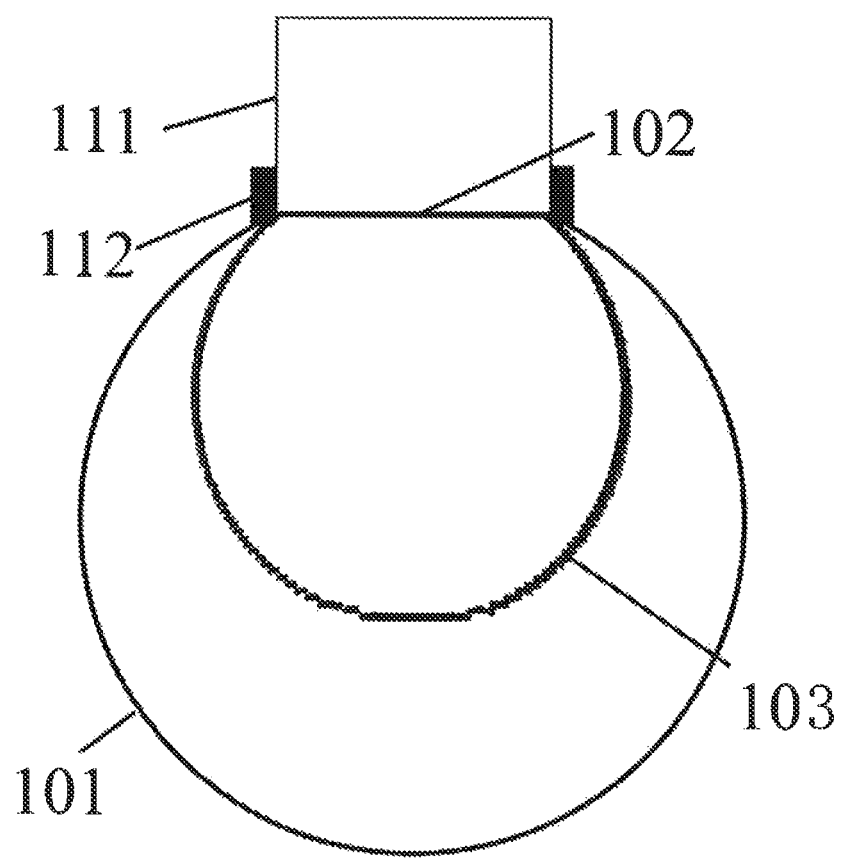
FIG. 2 is a schematic structural diagram showing a cystic applicator according to another exemplary embodiment of the present disclosure.

In other embodiments, as shown in FIG. 2, the collimator 111 and the housing 101 may be individual structures connected to the opening of the housing 101 through a connection structure such as a buckle 112, and the two may be separated and combined. Other aspects of the applicator shown in FIG. 2 are the same as those in FIG. 1 and will not be repeatedly described here.

Figure 3:
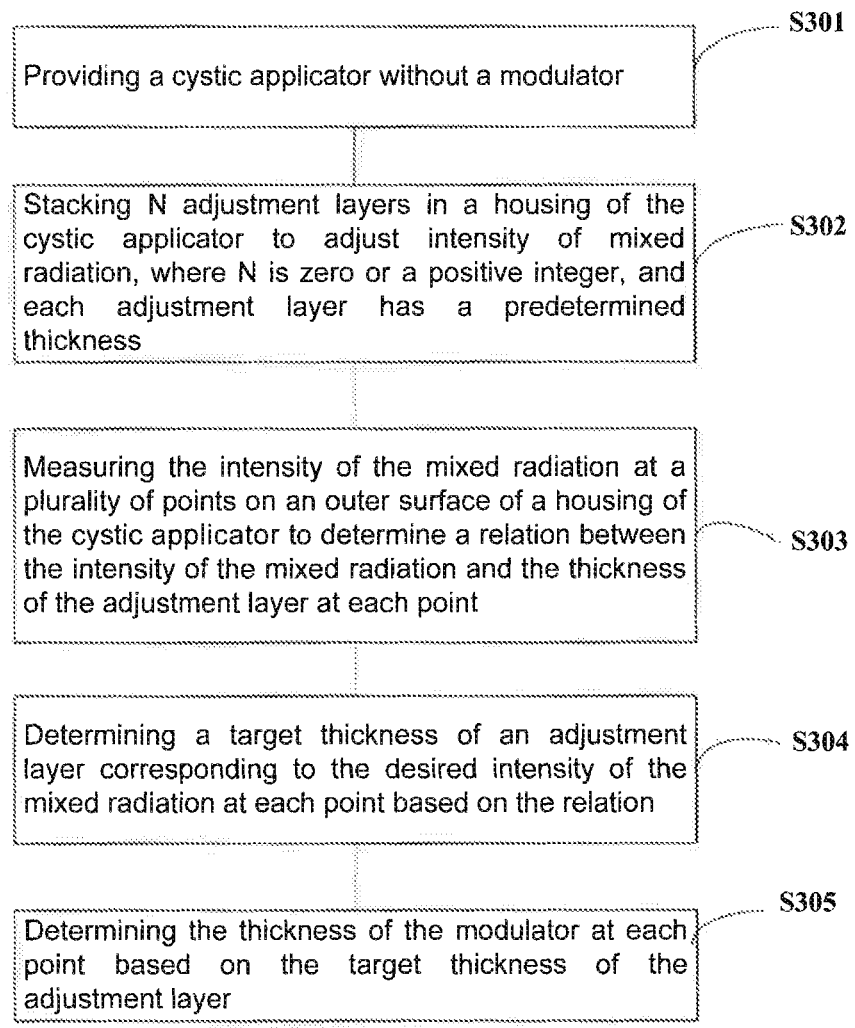
FIG. 3 shows a flow chart of a method for determining a thickness of a modulator in a cystic applicator according to an exemplary embodiment of the present disclosure.

FIG. 3 shows a flow chart of a method for determining a thickness of a modulator 103 in a cystic applicator according to an exemplary embodiment of the present disclosure. As shown in FIG. 3, the method may be started at step S301, providing a cystic applicator that does not include a modulator 103, i.e., the modulator 103 is not included in housing 101.

Next, in step S302, it may stack N adjustment layers in the housing 101 to adjust an intensity of the mixed radiation, where N is zero or a positive integer, and in step S303, determining the intensity of the mixed radiation at a plurality of points on an outer surface of the housing 101, thus determining a relation between the intensity of the mixed radiation at each point and the thickness of the adjustment layer.

Figure 4:
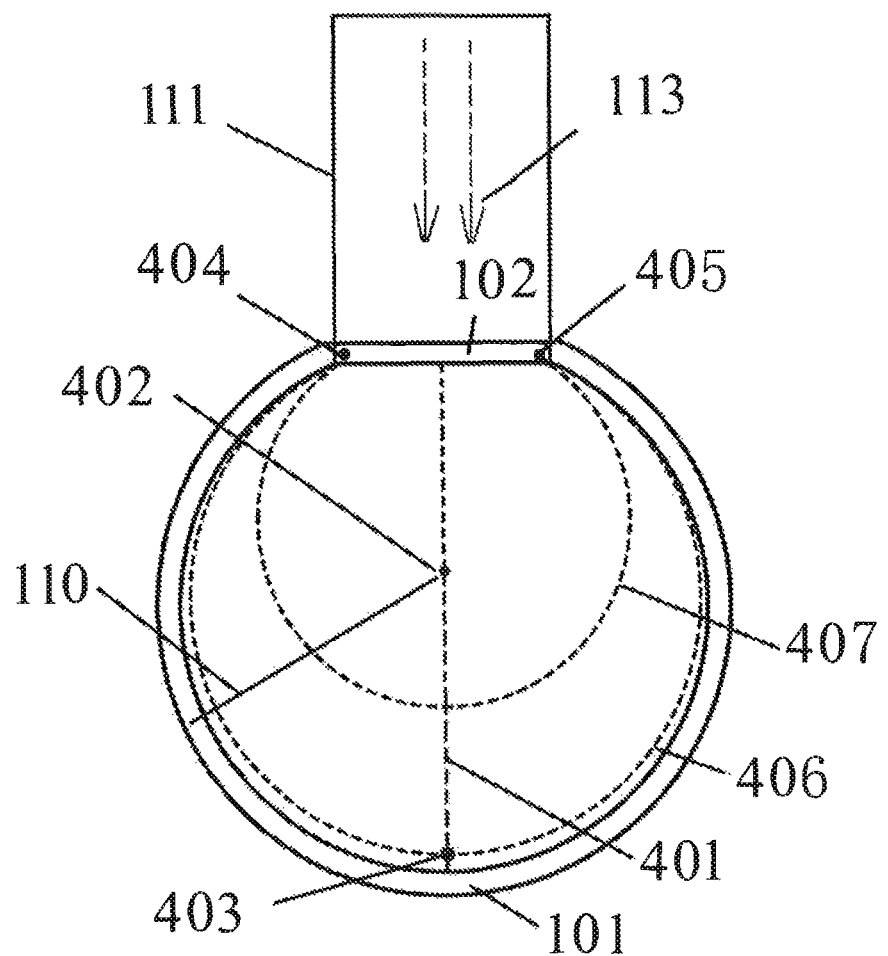
FIG. 4 shows a schematic diagram of an arrangement for an adjustment layer in a method for determining a thickness of a modulator according to an exemplary embodiment of the present disclosure.

FIG. 4 shows an example of a plurality of adjustment layers disposed in the spherical housing 101. As shown in FIG. 4, 113 is an incident direction of the electron beam, 401 is a central axis of the cystic applicator, 402 is a geometric center of the cystic applicator, i.e. a circle center of the spherical housing 101, 110 is a radial direction of the spherical housing 101, 403 is a point on the central axis 401, and 404 and 405 are two points respectively at the opening of the cystic applicator. Each adjustment layer has a predetermined shape and thickness, and it is a crescent in the example of FIG. 4, whose outer arc and inner arc pass through points 403, 404 and 405, and whose circle center is also on the central axis 401. For example, the arc forming the crescent may be the inner wall of the housing 101, or the arcs 406, 407, etc. In FIG. 4, the inner wall of the housing 101 is the outer wall of the first adjustment layer, the arc 406 is the inner wall of the first adjustment layer and is also the outer wall of the second adjustment layer, and the arc 407 is the inner wall of the N-th adjustment layer. The shape and thickness of each adjustment layer are known, and a thickness difference of 1 mm between each adjustment layer on the central axis may be set. The number of adjustment layers is related to the feature of radiation after it passes through the scattering foil 102, and the higher the energy of the radiation, the greater the intensity difference, and the greater thickness attenuation adjustment is required, therefore, the more adjustment layers are required.

The intensity of the mixed radiation at a plurality of points on the outer surface of the housing 101 may be determined when different numbers (e.g., 0, 1, 2, . . . , 10, and more) of adjustment layers are provided. For example, for the spherical housing 101, it may be considered that the radiation intensity is identical at points on the cross section of the housing 101 perpendicular to the central axis 401, therefore, the radiation intensity thereof may be determined by taking the points at different polar angles (taking a circle center as a pole point, a center axis 401 as a pole axis, such as an angle 505 shown in FIG. 5) on the housing 101, thus determining the relation between the intensity of the mixed radiation at each point and the thickness of the adjustment layer. FIG. 6 shows curves 601, 602, and 603 which respectively show the relationship between the radiation intensities and the thicknesses of the adjustment layer at three points where the polar angles on the housing 101 are 0 degrees, 30 degrees, and 60 degrees, respectively, wherein the scattering foil 102 is tungsten with a thickness of 0.5 mm, and the first radiation beam is an electron beam of 6 MeV. In FIG. 6, the dose is normalized to the dose at the adjustment layer 0, and the abscissa is the number of the adjustment layers, and it should be understood that each adjustment layer has a predetermined shape and thickness, therefore, the number of the adjustment layers may be easily converted into the thickness of the adjustment layer, which will be described below.

Determining the intensity of the mixed radiation at each point may be performed by various methods, for example, it may be performed by a physical measurement or by a simulation calculation. For example, under the attenuation and scattering conditions of each adjustment layer, the Monte Carlo simulation method may be used to calculate the dose at each point in a region outside the surface of housing 101.

Then, in step S304, based on the obtained relation between the thickness of adjustment layer and the radiation intensity, a target thickness of the adjustment layer corresponding to the desired mixed radiation intensity at each point may be determined. For example, if the desired radiation intensity is 80%, the thickness of the adjustment layer corresponding to 80% is determined, and further in step S305, determining a desired thickness of the modulator 103 at each point based on the determined target thickness of the adjustment layer.

For convenience of manufacture, the thickness of the modulator 103 may be expressed as the thickness angle distribution at different polar angles with the circle center 402 as the pole point and the central axis 401 as the polar axis, therefore, it is also necessary to calculate the thickness angle distribution of each adjustment layer in the polar coordinate system. The calculation method of a radial thickness of an adjustment layer will be described below with reference to FIG. 5.

Figure 5:
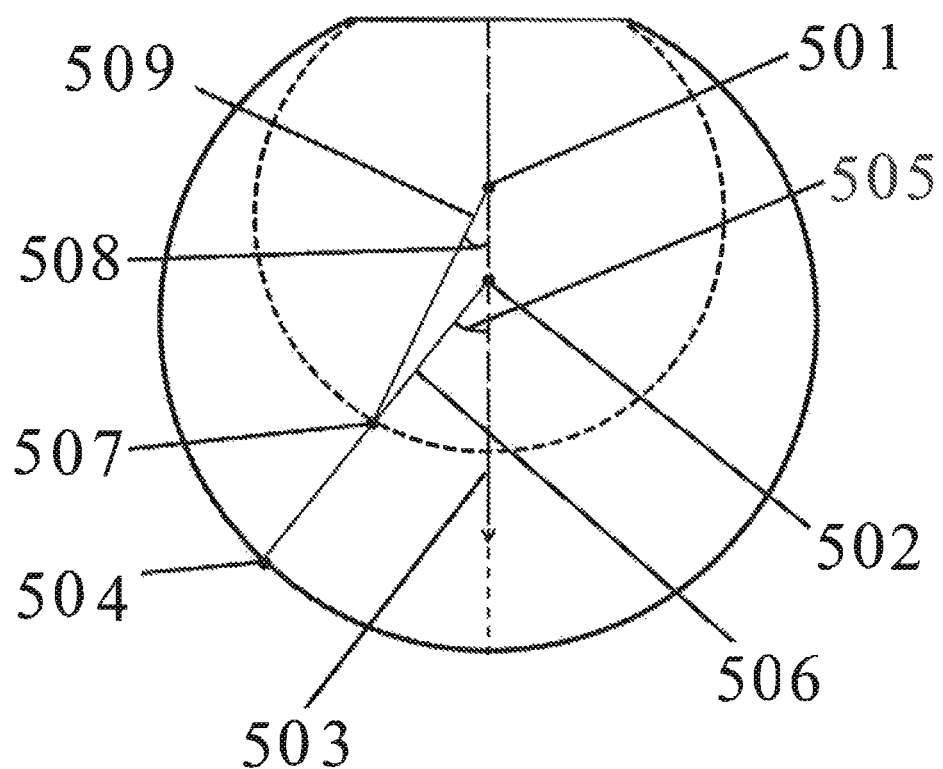
FIG. 5 shows a schematic diagram of a calculation method for a radial thickness of an adjustment layer.
Figure 6:
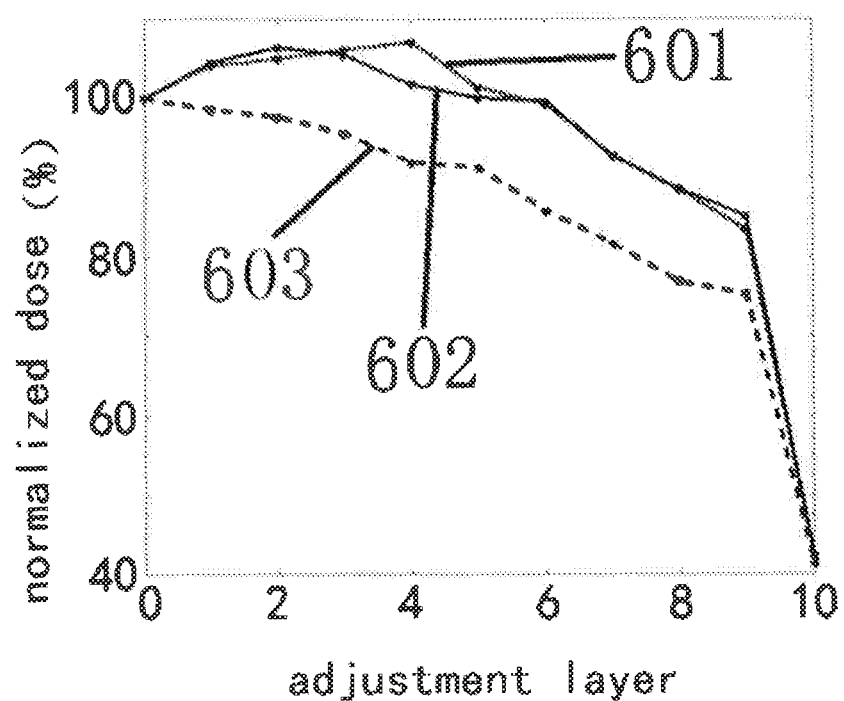
FIG. 6 is a relation showing the relationship between a dose at a point on a housing of a cystic applicator and a radial thickness of an adjustment layer.

As shown in FIG. 5, a point 501 is the geometric center $I_i$ of the i-th adjustment layer, a point 502 is the geometric center $I_0$ of the cystic applicator, i.e., the circle center of the spherical housing 101, and a point 504 is one point on the surface of the housing of the cystic applicator, 505 and 506 are the polar angle θ and the polar radius r of the point 504 in the polar coordinate system with the point 502 as the pole point and the direction indicated by dotted arrow 503 as the polar axis, respectively. 507 is an intersection point of the polar radius 506 and the i-th adjustment layer. 508 and 509 are the polar angle $\theta_i$ and the polar radius $r_i$ of the point 507 in the polar coordinate system with the point 501 as the pole point and the direction indicated by the dotted arrow 503 as the polar axis, respectively. The cumulative thickness $d_i$ of the i-th adjustment layer at the polar angle θ is calculated by the following formula 1:

$$d_i(r,\theta)=r-r_{i0} \quad (1).$$

In the formula 1, $r_{i0}$ is the polar radius of point 507 in a polar coordinate system with the point 502 as the pole point and the direction indicated by the dotted arrow 503 as the polar axis, When $\theta_i \in (3\pi/2, \pi/2)$, $$r_{i0}=\sqrt{(|r_i\cos\theta_i|-(I_i-I_0))^2+(r_i\sin\theta_i)^2} \quad (2),$$

When $\theta_i \in [\pi/2, \pi/2]$, $$r_{i0}=\sqrt{(|r_i\cos\theta_i|+(I_i-I_0))^2+(r_i\sin\theta_i)^2} \quad (3).$$

Therefore, according to the above formulas 1-3, accumulated radial thickness of the adjustment layers may be calculated when i adjustment layers are provided. It should be understood that i is not necessarily an integer here, but is a number of adjustment layers corresponding to the desired dose determined according to the curves in FIG. 6, which may be any value greater than or equal to zero. Therefore, in step S304, the target thickness of the adjustment layer at each point corresponding to the desired mixed radiation intensity may be determined, further in step S305, the desired thickness of the modulator 103 at each point is determined based on the determined target thickness of the adjustment layer. In some embodiments, the adjustment layer and the modulator 103 may be made of the same material, therefore, the desired thickness of the modulator is equal to the determined target thickness of the adjustment layer at each point. Of course, the adjustment layer and the modulator 103 may also be made of different materials, at this moment, the thickness of the adjustment layer needs to be converted into the thickness of the modulator according to the material property.

Figure 7:
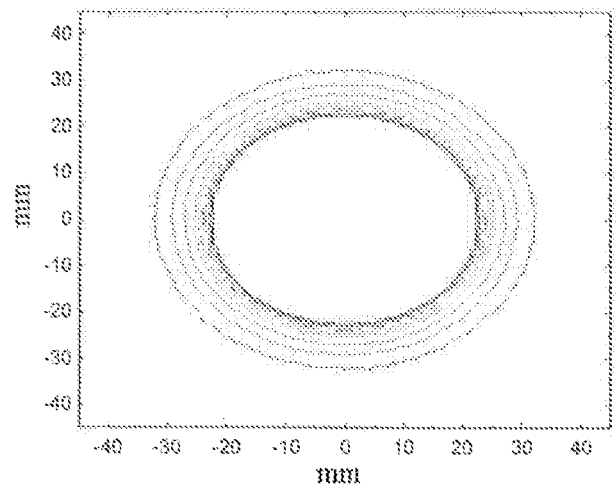
FIG. 7 shows a dose distribution of a coronal plane in a region outside the surface of the cystic applicator.

FIG. 7 shows a dose distribution of a coronal plane in a region outside the surface of the cystic applicator provided by the embodiment of the present disclosure. What is shown in the figure is a dose distribution on a coronal plane passing through a geometric center of the cystic applicator, wherein the geometric center of the cystic applicator is taken as the origin point, and the isodose line shown in the figure is drawn from 20% in a step of 20%. The dose distribution is uniform at the position equidistant from the surface of the cystic applicator, which is consistent with the geometric shape of the cystic applicator.

Figure 8:
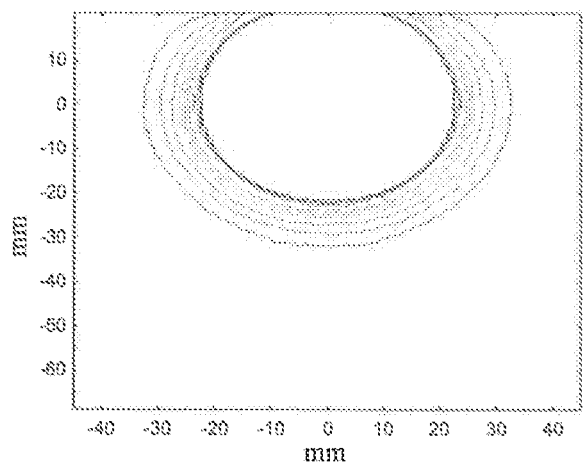
FIG. 8 shows a dose distribution of a cross-section in a region outside the surface of a cystic applicator.

FIG. 8 shows the dose distribution of a cross-section in a region outside the surface of the cystic applicator provided by the embodiment of the present disclosure. What is shown in the figure is a dose distribution on a cross section passing through a geometric center of the cystic applicator, wherein the geometric center of the cystic applicator is taken as the origin point, and the isodose line shown in the figure is drawn from 20% in 20% step. In a polar coordinate system with the point 502 as the pole point and the direction indicated by the dotted arrow 503 as the polar axis in FIG. 5, and in the range of 0° to 155° and 205° to 360°, the dose distribution is uniform at the position equidistant from the surface of the cystic applicator, which is consistent with the geometric shape of the cystic applicator.

Compared with the prior art, the cystic applicator provided by the present disclosure may convert a portion of an electron beam into X-rays, modulate the intensity of the mixed radiation (including the electron beam and X-rays), produce a uniform dose distribution in a region outside the surface of the cystic applicator, and be used for radiotherapy of the cystic tumor (including a saccular tumor, a tubular tumor and other cystic tumors), thus expand the application range of the electron beam.

The above description of the disclosed aspects is provided to enable any of those skilled in the art to make or use the present application. Various modifications to these aspects are very obvious for those skilled in the art, and the generic principles defined herein may be applied to other aspects without departing from the scope of the present application. Therefore, the present application is not intended to be limited to the aspects shown herein, but rather to present the broadest scope consistent with the principles and novel features disclosed herein.

The above description has been provided for the purposes of illustration and description. In addition, this description is not intended to limit the embodiments of the present application to the forms disclosed herein. Although various example aspects and embodiments have been discussed above, those skilled in the art will recognize certain variations, modifications, alterations, additions and sub-combinations thereof.

The invention claimed is:

1. An applicator for intraoperative radiotherapy comprising:
   a housing having a hollow structure with an opening, the housing being made of plastic and configured to be surrounded by a tumor region in a patient body to be irradiated and support the tumor region during the intraoperative radiotherapy;
   a scattering foil disposed at the opening of the hollow structure and configured to receive a first radiation and convert a portion of the first radiation into a second radiation while scattering the first radiation, the first radiation being electron beam radiation and the second radiation being X-ray radiation; and an intensity modulator disposed inside the housing, the intensity modulator being configured to modulate an intensity of mixed radiation including the first radiation and the second radiation so that the mixed radiation passes through an outer surface of the housing during the intraoperative radiotherapy.

2. The applicator of claim 1, wherein the scattering foil has a thickness that is optimized to ensure that the first radiation has a predetermined scattering angle while the mixed radiation has a predetermined intensity.

3. The applicator of claim 1, wherein the intensity modulator has a thickness that is optimized so that the mixed radiation has a desired intensity distribution on the outer surface of the housing.

4. The applicator of claim 1, wherein the housing is configured to support the scattering foil and the intensity modulator.

5. The applicator of claim 1, wherein the hollow structure has a spherical shape, a tubular shape, or an irregular shape corresponding to the tumor region to be irradiated.

6. The applicator of claim 1, further comprising:
a collimator connected to the opening of the housing, the first radiation being irradiated onto the scattering foil through the collimator.

7. The applicator of claim 6, wherein the collimator and the housing are formed as an integral structure.

8. The applicator of claim 1, wherein an outer surface of the intensity modulator contacts an inner surface of the housing.

9. The applicator of claim 1, wherein an outer surface of the intensity modulator is spaced apart from an inner surface of the housing.

10. The applicator of claim 1, wherein the housing is made of plexiglass.

11. The applicator of claim 1, wherein the housing is made of PMMA.

12. The applicator of claim 1, wherein the housing is made of polyester.

* * * * *